United States Patent [19]

Orlowski et al.

[11] 4,379,695
[45] Apr. 12, 1983

[54] DENTAL MATERIAL COMPRISING DIMETHYACRYLATE ADDUCTS OF GLYCIDYL METHACRYLATE WITH DIESTERS OF BIS(HYDROXYMETHYL) TRICYCLO[5.2.1.0$^{2,6}$]DECANE AND DICARBOXYLIC ACIDS

[75] Inventors: Jan A. Orlowski, Altadena; David V. Butler, West Covina; Patrick D. Kidd, San Dimas, all of Calif.

[73] Assignee: Scientific Pharmaceuticals, Inc., Duarte, Calif.

[21] Appl. No.: 267,609

[22] Filed: May 27, 1981

Related U.S. Application Data

[63] Continuation-in-part of Ser. No. 155,160, Jun. 2, 1980, Pat. No. 4,337,349.

[51] Int. Cl.$^3$ ............................................. A61K 6/08
[52] U.S. Cl. ..................................... 433/217; 106/35; 260/998.11; 433/199; 433/201; 433/202; 433/222; 433/228; 523/115
[58] Field of Search ................. 106/35; 433/199, 201, 433/202, 217, 228, 222; 260/998.11; 523/115

[56] References Cited
U.S. PATENT DOCUMENTS
4,172,951 10/1979 Gruber et al. ................., 560/84

*Primary Examiner*—Lorenzo B. Hayes
*Attorney, Agent, or Firm*—Cushman, Darby & Cushman

[57] ABSTRACT

Dimethacrylates are provided having the following chemical structure:

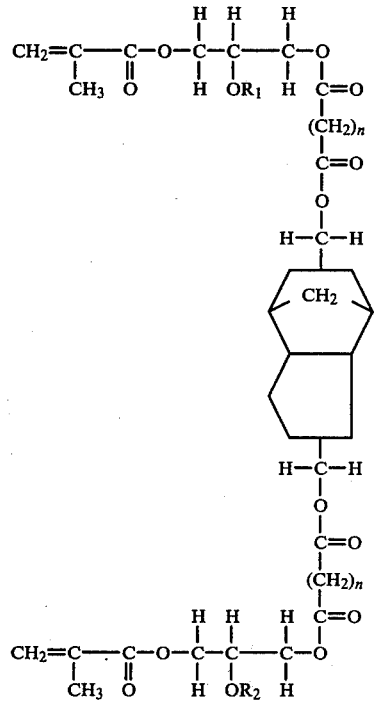

wherein
n represents a number of 2 to 8;
$R_1$ and $R_2$ are the same or different and are hydrogen or groups of the formula:

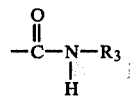

where
$R_3$ is an aliphatic, aromatic or cycloaliphatic group having 1 to 14 carbon atoms. These compounds are useful in dental material which cures to form polymers having high mechanical strength, low water sorption, resistance to staining, good color stability when exposed to short-wave radiation (e.g., sunlight) and good chemical resistance to the oral environment. Also provided are a method for polymerizing these compounds in situ on teeth and a tooth comprising polymers of these compounds.

13 Claims, No Drawings

DENTAL MATERIAL COMPRISING DIMETHYACRYLATE ADDUCTS OF GLYCIDYL METHACRYLATE WITH DIESTERS OF BIS(HYDROXYMETHYL) TRICYCLO[5.2.1.0²,⁶]DECANE AND DICARBOXYLIC ACIDS

CROSS REFERENCE TO OTHER CASES

This is a continuation-in-part of application Ser. No. 155,160 filed June 2, 1980 U.S. Pat. No. 4,337,349.

BACKGROUND OF THE INVENTION

The present invention relates to a polymerizable compound, a polymer formed from this compound, a dental material containing this compound, a method for polymerizing this compound in situ on teeth, and a tooth comprising a polymer of this compound.

In recent years, the use of polymer-based dental materials became very prominent as they improved aesthetics and durability of restorations, faciliated application techniques and allowed great expansion of dental techniques in restorative, corrective and preventive applications. Especially important became filled restorative material, cements, bonding agents, fissure sealers and orthodontic adhesives based on the polymerizable in situ aromatic and aliphatic methacrylates. The best properties in these materials have been obtained when the resin part of the composition is comprised of one or more of the following monomers:

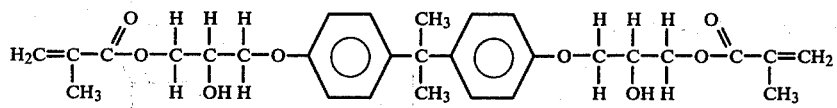

i.e., 2,2-bis [4'(3"-methacroyl-2"-hydroxypropoxy)phenyl] propane (known in the industry as Bis-GMA), its adducts with various alkyl-isocyanate, such as adducts described in the Waller U.S. Pat. No. 3,629,187, the entire disclosure of which is hereby incorporated by reference and relied upon, and

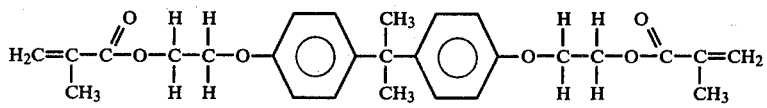

i.e., 2,2-bis[4'(2"-methacroylethoxy)phenyl] propane (known in the industry as EBA).

These high molecular weight monomers are usually diluted with lower molecular weight polymethacrylates including dimethacrylates such as di-, tri- or tetraethylene glycol dimethacrylate, 1,6-hexanediol dimethacrylate, or trimethacrylates such as trimethylolpropane trimethacrylate. Other methacrylate monomers known to be used in certain restorative materials, cements, fissure sealers, bonding agents or orthodontic adhesives and claimed to improve mechanical, physical, clinical or aesthetic properties of materials are:

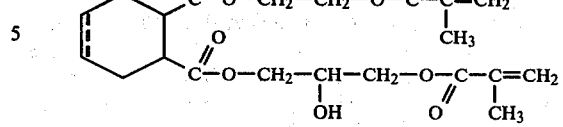

i.e., 2-methacroylethyl-3-methacroyl-2-hydroxypropyl tetrahydro (or hexahydro) phthalate and

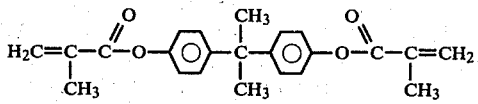

i.e., 2,2 bis(4'-methacroylphenyl)propane (known in the industry as BADM).

In an attempt to improve methacrylate resin based dental materials, research efforts have been concentrated mainly on reducing their water sorption, as related to susceptibility to hydrolysis and staining, on monimizing their polymerization shrinkage and on improving their resistance to discoloration when exposed to sunlight.

These properties depend on the chemical structure of the monomer or monomers used in the formulation and their purity. In the formulations containing (besides the resin binder) a solid phase in the form of dispersed filler particles, the viscosity of the resin constitutes another important factor. The lower the viscosity of the alternative monomers that may be used in the formulation, other properties remaining similar or the same, the more filler may be incorporated in the formulation contributing to lower shrinkage, lower water sorption, better wear resistance and overall improved mechanical properties.

As it is recognized in the dental profession, the composite restoratives known up to now were unsuitable in most instances for use in posterior restorations, mainly because of their unsatisfactory wear resistance. This is especially true for Class II restorations as exposed the most to strong mastication forces. The typical properties of composite restoratives made according to presently known techniques are given below:

| | |
|---|---|
| Water Sorption as 37° C. | 0.7 mg/cm² |
| Compressive Strength | 30,000–40,000 psi |
| Diametral Tensile Strength | 3,480–4,600 psi* |
| Color Stability | Discoloration perceptible with difficulty |
| Hardness (Barcol) | 98 |

Opacity/Translucency 0.35–0.55*
Filler/Resin ratio by Weight 3.2:1 to 4.2:1

* Determined according to American Dental Association Specification No. 27, JADA, Vol. 94, June, 1977.

In addition to the above-mentioned Waller U.S. Pat. No. 3,629,187, various polymeric dental materials have been described in the following U.S. Pat. Nos. 3,066,112 (Bowen); 3,179,623 (Bowen); 3,194,783 (Bowen); 3,194,784 (Bowen); 3,539,533 (Lee II et al); 3,541,068 (Taylor); 3,597,389 (Taylor); 3,721,644 (Stoffey et al); 3,730,947 (Stoffey et al); 3,751,399 (Lee, Jr. et al); 3,766,132 (Lee, Jr. et al); 3,774,305 (Stoffey et al); 3,860,556 (Taylor); 3,926,906 (Lee, II et al); 4,102,856 (Lee, Jr.); and 4,107,845 (Lee, Jr. et al) and 3,862,920 (Foster et al). Further information on polymer based dental materials is given on pages 501–508 and 515–517 of the *Kirk-Othmer Encyclopedia of Chemical Technology*, Third Edition, Volume 7 (1979). The entire disclosures of the patents and the Kirk-Othmer reference set forth in this paragraph are hereby incorporated by reference and relied upon.

An important improvement in clinical performance of polymer-based dental restoratives may be achieved and their scope of applications greatly expanded if their water sorption is lowered, mechanical strength and hardness improved and filler/resin ratio significantly raised. Accordingly, there is a need in the art to develop polymerizable compounds which tend to overcome the shortcomings of the prior art polymerizable compounds used in dental materials.

SUMMARY OF THE INVENTION

The present invention relates to a compound of the following formula:

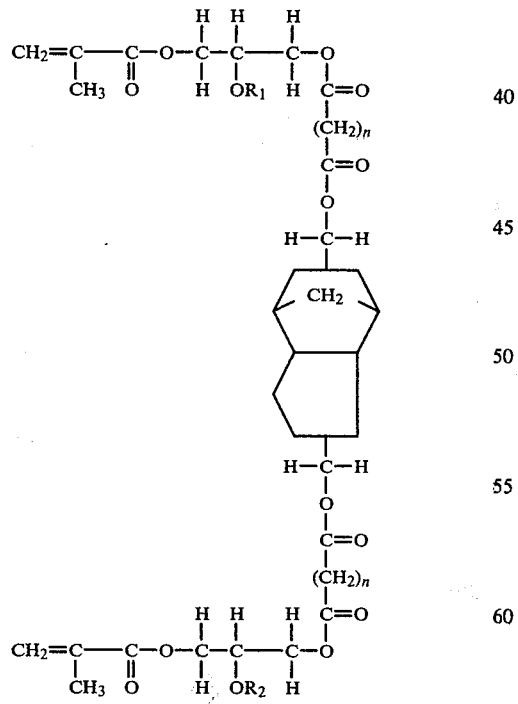

where n represents a number of 2 to 8;

$R_1$ and $R_2$ are the same or different and are hydrogen or groups of the formula

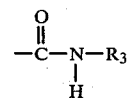

where $R_3$ is an aliphatic, aromatic or cycloaliphatic group having 1 to 14 carbon atoms.

Other aspects of this invention relate to a polymer formed from this compound, a dental material (e.g., particularly a composite restorative material) containing this compound, a method for polymerizing this compound in situ on teeth and a tooth comprising a polymer of this compound.

DETAILED DESCRIPTION OF THE INVENTION

This invention relates to a dimethacrylate compound represented by the structure:

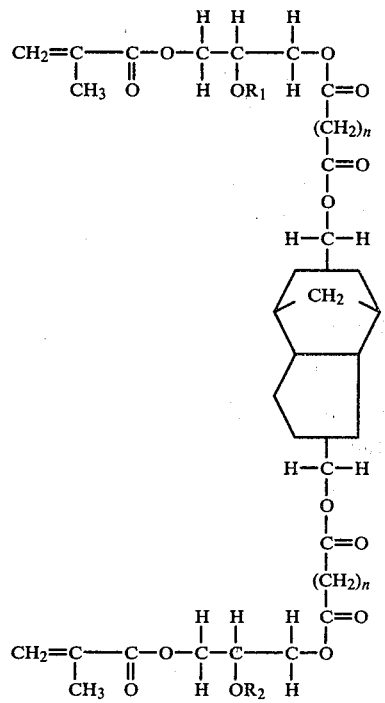

where n represents a number of 2 to 8;

$R_1$ and $R_2$ are the same or different and are hydrogen or groups of the formula:

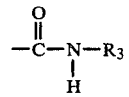

where $R_3$ is an aliphatic, aromatic or cycloaliphatic group having 1 to 14 carbon atoms. Dimethacrylate compounds of this formula are referred to herein as compounds of the present invention.

The relative positioning of carbon atoms and substituents in the tricyclo [5.2.1.0$^{2,6}$]decane group of the above formula may be shown in the following structure:

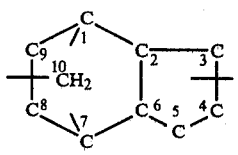

Accordingly, it can be seen that the tricyclo[5.2.1.0²,⁶]-decane group is substituted in 2 positions. More particularly, one substituent is attached to the tricyclo[5.2.1.0²,⁶]decane group at the 3, 4 or 5 position (preferably the 3 or 4 position), whereas the other substituent is attached to the tricyclo[5.2.1.0²,⁶]decane group through either the 8 or 9 position. Thus, the formula for the compound of the present invention connotes various isomers with respect to the positioning of substituents from the tricyclo[5.2.1.0²,⁶]decane group, as well as mixtures of these isomers. It will further be understood that structures given herein are intended to connote all possible stereoisomers and combinations thereof.

Although not intending to be strictly limited to any particular means for forming the compounds of the present invention, it is noted that these compounds may be described as adducts of glycidyl methacrylate with diesters of bis(hydroxymethyl) tricyclo[5.2.1.0²,⁶]decane and dicarboxylic acids. Thus, for example, a dicarboxylic acid represented by the formula:

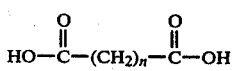

where n is 2 to 8, may be reacted with a bis(hydroxymethyl) tricyclo[5.2.1.0²,⁶]decane represented by the formula:

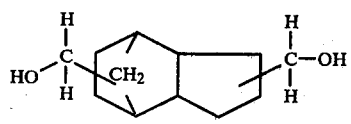

to form a diester intermediate having two terminal carboxylic acid groups, said diester represented by the formula

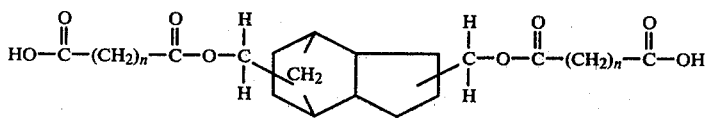

where n has the meaning defined above. Examples of dicarboxylic acids for this esterification reaction include succinic acid, glutaric acid, adipic acid, pilmelic acid, suberic acid, azelaic acid and sebacic acid. Preferred bis(hydroxymethyl) compounds for use in the above-mentioned esterification reaction are 3,8-bis(hydroxymethyl)tricyclo[5.2.1.0²,⁶]decane, 4,9-bis(hydroxymethyl)tricyclo[5.2.1.0²,⁶]decane and mixtures of these isomers. This esterification reaction may conveniently take place in an excess of the dicarboxylic acid reactant, such as by a dropwise addition of the bis(hydroxymethyl) compounds to the dicarboxylic acid, to avoid the possibility of a polycondensation side reaction taking place.

The above-mentioned diester intermediate may then be reacted with glycidyl methacrylate to give a compound represented by the formula:

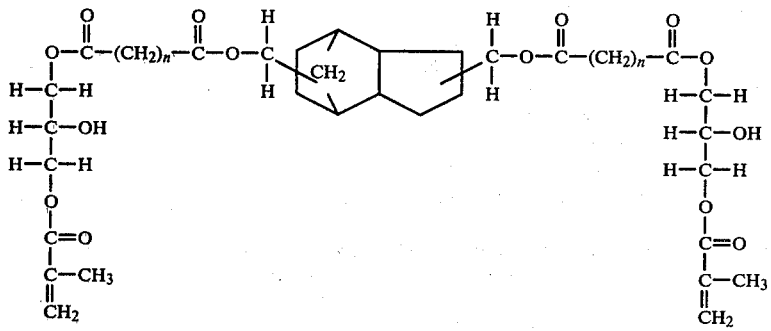

which corresponds to a dihydroxy compound of the present invention, wherein both $OR_1$ and $OR_2$ are hydroxy groups. This dihydroxy compound may then be converted to further compounds of the present invention, e.g., mono- and/or dicarbamates of this dihydroxy compound, by reacting same with isocyanates of the formula $$R_3-N=C=O$$

where $R_3$ has the meaning defined above, i.e., an aliphatic, aromatic or cycloaliphatic group having 1 to 14 carbon atoms, e.g. hydrocarbon groups or haloaryl groups such as chloroaryl groups. Examples of groups represented by $R_3$ include methyl, ethyl, n-butyl, isoamyl, n-amyl, hexyl, n-octyl, isooctyl, dodecyl, tetradecyl, phenyl, p-ethyl benzyl, p-tolyl, p-butylphenyl, xylyl, -napthyl, p-chlorophenyl, benzyl, cyclopentyl, m-chlorophenyl and cyclohexyl. A preferred group represented by $R_3$ is n-butyl. As hydrocarbon groups for $R_3$ there can be used for example, alkyl, aryl, aralkyl and cycloalkyl.

As mentioned previously, the dimethylacrylates of the present invention may be formed by reacting a diester intermediate with glycidyl methacrylate. To facilitate the formation of this diester intermediate, a suitable condensation catalyst, such as dibutyltin diacetate, may be used. The diester intermediate having two terminal carboxylic acid groups may then be reacted with glycidyl methacrylate in the presence of a suitable electron donating catalyst such as triphenylphosphine and a polymerization inhibitor such as butylated hydroxytoluene (BHT). More information on reactions of carboxylic acids with epoxides may be found in H. Frankel-Conrat and H. S. Olcott, J. Am. Chem. Soc. 66, 1420 (1944). Reaction of the adduct of the diester intermediate and glycidyl methacrylate with various proportions of isocyanates may produce, e.g., various mixtures of two or more of the above-mentioned adduct, monocarbamates and dicarbamates.

The dimethacrylates of the present invention may be combined with other polymerizable unsaturated materials, such as acrylic or methacrylic monomers or prepolymers, and polymerized. Thus, the dimethacrylates of the present invention may be polymerized to form either homopolymers or copolymers, e.g., containing at least 10% by weight of these dimethacrylate moieties. Preferably, copolymers of the dimethacrylates of the present invention may contain at least 40% by weight of these dimethacrylate moieties. As used herein, the term "moiety" shall connote an entire repeating polymeric unit and not some lesser fragment thereof.

Polymers of the dimethacrylates of the present invention are characterized in that they may have a high degree of crosslinking. Accordingly, these dimethacrylates may be added to mono-functional acrylic and methacrylic monomers and polymerized to form crosslinked polymers. Examples of these acrylic and methacrylic compounds include acrylic and methacrylic acid and esters thereof with alcohols containing, e.g., 1 to 4 carbon atoms. Examples of such acrylic and methacrylic esters include methylmethacrylate, ethylmethacrylate, butylmethacrylate, methylacrylate, ethylacrylate and butylacrylate.

Copolymers having an even higher degree of crosslinking may be produced by copolymerizing the dimethacrylates of the present invention with other polyfunctional acrylic ester or methacrylic ester monomers, i.e., monomers containing two or more acrylic or methacrylic functionalities. One class of these polyfunctional monomers includes monomers which are used as diluents in dental materials. Such polyfunctional acrylic ester or methacrylic ester monomers include alkylene glycol diacrylates, alkylene glycol dimethacrylates, polyalkylene glycol diacrylates, polyalkylene glycol dimethacrylates, alkanetriol triacrylates and alkanetriol trimethacrylates, e.g., containing from 8 to 18 carbon atoms. Examples of such monomers include ethylene glycol dimethacrylate, di-, tri- or tetraethylene glycol dimethacrylate, 1,6-hexanediol dimethacrylate, the dimethacrylate formed by the reaction of methacrylic acid with butanediol, trimethylolpropane trimethacrylate and the acrylic esters corresponding to these methacrylates, e.g. ethylene glycol diacrylate. As far as polyfunctional acrylates and methacrylates are concerned, these monomers are characterized by relatively low molecular weight (e.g., 339 or less) and low viscosity. The above-mentioned polyglycol dimethacrylates are further characterized by low surface tension.

Another class of polyfunctional acrylates and methacrylates includes the relatively high molecular weight (e.g., 364 or more) acrylic or methacrylic monomers used in dental compositions. Such polyfunctional compounds include, especially, dimethacrylates such as 2,2-bis[4'(3''-methacroyl-2''-hydroxypropoxy)phenyl]propane. (i.e. Bis-GMA), 2,2-bis[4'(2''-methacroylethoxy)phenyl]propane (i.e., EBA), 2-methacroylethyl-3-methacroyl-2-hydroxypropyl tetrahydrophthalate, 2-methacroylethyl-3-methacroyl-2-hydroxypropyl hexahydrophthalate and 2,2-bis(4'-methacroylphenyl)propane (i.e. BADM). Further polyfunctional monomers containing up to four acrylic or methacrylic functionalities are described in the Stoffey et al U.S. Pat. No. 3,721,644, the entire disclosure of which is hereby incorporated by reference and relied upon.

Accordingly, copolymers may be formed from polymerizable materials comprising at least one dimethacrylate of the present invention and, e.g., at least 10% by weight of one or more of the copolymerizable materials described herein.

Polymerization of the dimethacrylates of the present invention may be initiated by known means for initiating the polymerization of dimethacrylates such as heat, chemical means or electromagnetic irradiation. Thus, in order to induce curing of dimethacrylates, a free-radical catalyst may be incorporated therein. Organic peroxide initiators, such as methyl ethyl ketone peroxide, t-butyl peroctoate, iso-propyl percarbonate, cumene hydroperoxide, dicumyl peroxide, and especially benzoyl peroxide, are preferred.

The ability of the initiator to cure dimethacrylates may be enhanced through the use of activators or accelerators. Thus, a peroxide initiator can be activated with a tertiary aromatic amine such as N,N-dimethyl-p-toluidine or N,N-bis(2-hydroxyethyl)-p-toluidine.

The amount of free-radical catalyst may be selected according to the curing rate desired. For instance, if a relatively slow curing rate is desired, a minimum catalytically effective amount, such as 0.5% by weight based on the polymerizable components, may be selected. On the other hand, when faster rates of cure are desired, greater amounts of free-radical catalyst, such as 4.0% or more by weight based on the polymerizable components, may be selected. Accordingly, the amount of catalyst may range from about 0.5 to about 4.0% by weight based upon the weight of the polymerizable components.

As with the free-radical catalyst, the amount of the activator selected may vary, e.g., from about 0.5 to about 4.0% by weight of the polymerizable components, depending upon the desired curing rate.

Polymerization of the dimethacrylates of the present invention may also be initiated by ultraviolet or visible light using known light activated polymerization initiators such as benzoin, benzoin methyl ether, benzil and other commercially available photoinitiators. For example, one may select from about 1% to about 5% by weight based on the polymerizable components of a sensitizer capable of initiating polymerization when exposed to UV light between about 3550 A. to about 3720 A.

The various components of a material containing a dimethacrylate of the present invention may be combined in any suitable manner. However, since chemically initiated polymerization starts immediately upon admixture of all three of (1) a methacrylate, (2) an initiator and (3) an activator, it is necessary to separate at least one of these components from the others until immediately before polymerization of the methacrylate. This separation may be achieved through the use of a two-package product, wherein various components of a material containing a dimethacrylate of the present invention are separately contained until the time of polymerization.

Therefore, the components of such a composition may be separated by means of a two-package product into two parts, one part containing the polymerization initiator and the other part containing the polymerization accelerator.

It is helpful to package polymerizable methacrylates with inhibitors, such as butylated hydroxytoluene (BHT) or hydroquinone methyl ether. Thus, BHT may be included in an amount from about 0.1 to about 0.3% by weight based on the polymerizable components to increase the storage stability of these polymerizable components.

Ultraviolet stabilizers such as 2-hydroxy-4-methoxybenzophenone (Cyasorb UV-9, a tradename of American Cyanamide) may be included to enhance the stability of the polymerizable components as well as polymers resulting therefrom. For example, from about 0.4 to about 1.6% by weight of Cyasorb UV-9 based on the weight of the polymerizable components may be used for this purpose.

In addition to polymerizable unsaturated material, inorganic or polymeric fillers may also be added to the monomers of the present invention prior to polymerization of these monomers. Accordingly, the term "polymer" as used herein may connote a polymeric matrix material which binds together various fillers.

Up to about 6.5 parts or even up to 8.5 parts of filler material per part of polymerizable unsaturated material may be included. Particular inorganic filler materials include silica materials (e.g., powdered quartz, barium glasses, borosilicate glasses, $SiO_2$, fumed silica and lithium aluminum silicate) and alumina materials (e.g., $Al_2O_3$). These inorganic filler materials may be treated with coupling agents, such as [3-(methacroyl)propyl] trimethoxysilane, in order to assure the proper incorporation of filler into the polymeric matrix of the cured product. Other materials such as pigments may also be included in polymerizable materials comprising the dimethacrylates of the present invention.

It is noted that by varying the nature and proportions of curable compositions comprising one or more dimethacrylates of the present invention, a variety of such curable compositions as well as a variety of cured compositions resulting therefrom may be obtained. For example, curable compositions containing a relatively large amount of fillers, and relatively small amounts of low viscosity acrylic or methacrylic diluents, as well as minimum amounts catalysts and activators, may have a thick, doughlike consistency and a slow curing rate permitting working of the composition by molding and shaping before setting occurs. On the other hand, compositions containing little or no filler and relatively large amounts of low viscosity diluents, catalysts and accelerators may be flowable and fast curing, permitting brush-on application where little or no molding or shaping is required.

Polymerizable materials containing dimethacrylates of the present invention may now be described by way of examples of various dental materials. In this regard, composite restorative materials are given particular emphasis.

COMPOSITE RESTORATIVE MATERIALS

Composite restorative materials, as the name implies, is a composite material of a polymerizable material and a suitable filler. These materials are capable of curing in situ on teeth to restore a hardened surface thereto. These materials are generally applied as a filling material to prepared or drilled teeth. Accordingly, composite restorative materials should be of a thick, workable consistency suitable for application to a prepared tooth and capable of being shaped or molded thereon before setting occurs. Thus, composite restorative materials are relatively slow curing.

The thick consistency of composite restorative materials, as well as the desirable properties of the cured product formed from these materials, are largely a function of the relatively large amounts of filler materials employed therein. More particularly, composite restorative materials may contain glass or ceramic fillers in excess of the polymerizable material employed therein.

When the polymerizable material of the composite restorative contains one or more dimethacrylate monomers of the present invention, the weight ratio of filler to polymerizable material may range from about 1.5:1 to about 6.5:1 or even up to about 8.5:1 and, most especially, from about 4:1 to about 6:1. Suitable ceramic or glass fillers include silica materials, such as powdered quartz, barium glasses, borosilicate glasses, $SiO_2$ and lithium aluminum silicate, and alumina materials, such as $Al_2O_3$. Since composite restorative materials must be capable of conforming to the confined space of prepared tooth and hardening therein to achieve restorative properties, the particle size of these fillers must be sufficiently small. Generally, the particle sizes of these fillers may range from about 1 to about 150 microns, preferably from about 1 to about 40 microns. The average particle size of these fillers is preferably less than about 25 microns. Suitably, composite restorative materials may contain a mixture of two or more fillers, such as a mixture of a ceramic filler (e.g. powdered quartz) and glass filler (e.g., powdered glass).

According to techniques well known in the art, the fillers of composite restorative materials may be treated with one or more organosilane coupling agents. These coupling agents are also sometimes referred to as finishing or keying agents and include materials such as [3-(methacroyl)propyl]trimethoxysilane. A sufficient coupling amount of such coupling agent may be a small amount such as from about 0.5 to about 1.0 part of coupling agent per 100 parts of filler. Methods for treating fillers with coupling agents are described, for example, in U.S. Pat. No. 3,066,112 (Bowen), wherein an aqueous solution of tris(2-methoxyethoxy)vinyl silane is catalyzed with sodium hydroxide to give a pH of 9.3 to 9.8, and the filler is treated with this solution, for example, one-half percent of silane per weight of fused quartz. A slurry so formed is dried at about 125° C. and cooled. Another technique for treating filler with a coupling agent is described in the passage extending from column 3, line 40 to column 4, line 4 of U.S. Pat. No. 3,862,920 (Foster et al).

As indicated previously, the filler, rather than polymerizable material, constitutes a major portion of the composite restorative material. Perhaps for this reason the polymerizable material in composite restoratives is sometimes referred to as a "binder".

The polymerizable materials for forming a composite restorative material may contain at least two monomeric components, termed herein a first monomer and a second monomer. This first monomer is at least one dimethacrylate monomer according to the present invention, and the second monomer is at least one relatively low molecular weight diluent monomer which, among other purposes, serves to reduce the overall viscosity of the composite restorative materials.

The first monomer of the polymerizable material may be present in an amount of from about 20 to about 90% by weight, preferably from about 35 to about 45% by weight, of the polymerizable material. The second monomer may be present in an amount from about 10 to about 80%, preferably from about 15 to about 25% by weight, of the polymerizable material.

As a second monomer, an acrylic or methacrylic diluent, which is used for this purpose in dental materials, may be selected. More particularly, this diluent may be a di- or trimethacrylate having from 10 to 18 carbon atoms. Diluents falling within this class of compounds include relatively low molecular weight (e.g., 339 or less) alkylene glycol dimethacrylates, polyalkylene glycol dimethacrylates and alkanetriol trimethacrylates. Particular examples of such diluents include di-, tri- or tetraethylene glycol dimethacrylate, 1,6-hexanediol dimethacrylate, and trimethylolpropane trimethacrylate. Triethylene glycol dimethacrylate is a preferred diluent.

The polymerizable material of composite restoratives may also contain at least one third monomer. This third monomer may be a relatively high molecular weight (e.g., 364 or more) polyfunctional acrylic or methacrylic monomer used in dental compositions. Such polyfunctional compounds include dimethacrylates such as 2,2-bis[4'(3''-methacroyl-2''-hydroxypropoxy)-phenyl]propane (i.e. Bis-GMA), 2,2-bis[4'(2''-methacroylethoxy)phenyl]propane (i.e., EBA), 2-methacroylethyl-3-methoacroyl-2-hydroxypropyl tetrahydrophthalate, 2-methacroylethyl-3-methacroyl-2-hydroxypropyl hexahydrophthalate and 2,2-bis(4'-methacroylphenyl)propane (i.e. BADM).

Although the third monomer constitutes a different class of materials than the first monomer, the first monomer and third monomer serve similar functions. Therefore, the third monomer may be used as a replacement for a portion of the first monomer, provided that the polymerizable material contains at least 20% by weight of the first monomer. This third monomer may be used in quantities close to the quantities of first monomer. For example, the weight ratio of the first monomer to the third monomer may range from about 7:9 to about 9:7. Accordingly, when the first monomer is present in an amount ranging from about 35 to about 45% by weight of the polymerizable material, the third monomer may also be present in an amount ranging from about 35 to about 45% by weight of the polymerizable material. Preferably, however, the weight percent of the first monomer is greater or equal to the weight percent of the third monomer.

In describing various composite restorative compositions, mention has been made of various specific compounds, such as triethylene glycol trimethacrylate and Bis-GMA, which fall into classes of compounds referred to as a second monomer or third monomer. However, it will be understood that the polymerizable material of the composite restorative material may contain further compounds which may fall within these categories of second or third monomers and/or may even fall in some separate and distinct category. For example, the polymerizable material may contain a small amount of methacrylic acid. However, due to the objectionable odor and properties of methacrylic acid, this monomer should not be present in quantities in excess of about 2% by weight (e.g., between about 1 and 2% by weight of the polymerizable material).

Composite restorative compositions may be cured by any suitable means, a chemically initiated system being preferred. This initiating system involves the use of a catalyst and an accelerator. Peroxide catalysts such as benzoyl peroxide and tertiary amine accelerators such as N,N-bis(2-hydroxyethyl)-p-toluidine are preferred. The amounts of catalyst and accelerator may each be from about 0.5 to about 2.0% by weight of the polymerizable materials.

Desirably, initial curing of the composite restorative material should take place in about 1 to about 2 minutes upon admixture of the components thereof in order to permit adequate mixing and manipulation of these components outside the mouth prior to application to a prepared tooth. However, final curing is desirably delayed for 4 to 6 minutes from the initial contacting of restorative components in order to permit proper molding and shaping inside the mouth. It is noted that template structures are sometimes used in this molding process. Composite restorative materials having such curing characteristics may enable a dentist to perform a complete restoration of a prepared tooth within about ten minutes, including grinding and polishing the restorative material after final setting.

Composite restorative materials may be packaged in any suitable manner. Preferably, a two-package system is used wherein each package contains filler and polymerizable material in roughly equal amounts, one package containing the catalyst and the other package containing the accelerator. However, other systems are also possible. For example, according to another two-package system, one package may contain both filler and catalyst and the other package may contain polymerizable material and accelerator. Another system involves packaging together each of the components excluding the catalyst component. When this system is used, polymerization can be initiated by introducing catalyst dropwise from a stock solution thereof. Such a stock solution is described in the Taylor U.S. Pat. No. 3,541,068 (Note particularly column 6, lines 23–50).

Whatever packaging system is used, it is helpful to package polymerizable materials with one or more polymerization inhibitors such as BHT in order to enhance storage life. Also, shelf life of components containing accelerators may be improved by removing traces of peroxides from these components with a reducing agent.

Cured composite restoratives containing at least one monomer according to the present invention have desirable properties and may be capable of holding up under strong mastication forces. For instance, these materials may have a water sorption at 37° C. of less than 0.5 mg/cm$^2$ (preferably 0.4 mg/cm$^2$ or less), a compressive strength of greater than 40,000 psi (preferably 42,000 psi or more); a diametral tensile strength of greater than 5,000 psi (preferably 6,000 psi or more) and a hardness (Barcol) of greater than 98 (preferably 100 or more).

While particular emphasis has been devoted herein to the use of the monomers of the present invention in composite restorative materials, it will be understood that these mnomers may also be used in other dental materials. Examples of these other dental materials are given in the Waller U.S. Pat. No. 3,629,187 (Note particularly column 11, line 26 to column 15, line 36) and in the *Kirk-Othmer Encyclopedia of Chemical Technology*, Third Edition, Volume 7 (1979), pages 501–508 and 515–517. Waller characterizes these materials as, e.g., dental cements, dental cavity liners and dental lacquers. Kirk-Othmer characterizes these materials as, e.g., unfilled tooth-restorative resins, pit and fissure sealants and adhesives.

In addition to one or more monomers according to the present invention, dental materials may contain one or more of the copolymerizable materials described herein, provided that such copolymerizable material is acceptable for oral application associated with dental treatment. Particular examples of such copolymerizable material include those methacrylate monomers mentioned herein with respect to composite restorative materials. The fillers described herein with respect to composite restorative materials may also be used in certain other dental materials.

Certain dental materials may contain various amounts of filler, while other dental materials contain no filler at all. For instance, the dental cements described in the Waller U.S. Pat. No. 3,629,187 may contain little or no filler if a transparent cement is desired, but these cements may contain up to about a 1:1 ratio of filler to polymerizable material if a translucent cement is acceptable. It is noted that fillers used in dental cements generally have smaller particle sizes (e.g., an average particle size of 10 microns or less) with respect to fillers used in composite restorative materials.

Dental materials containing little or no fillers may be cured by a photoinitiation technique using known light polymerization initiators such as benzoin. Dental materials may also be cured with chemically initiated systems including those systems using sulfinic acid activators.

In addition to fillers and polymerizable material, dental materials may contain other substances. For instance, pigments may be included. Also, ultraviolet absorbers or stabilizers may be included to lessen discoloration of the cured material. Furthermore, fluorides, bacteriostatic agents and antibiotics may also be included.

Dental materials may be applied to teeth in a variety of manners depending upon the nature of the material and the desired use. For instance, thick, slow-curing materials, such as composite restoratives, may be molded and shaped in the mouth before final curing takes place. On the other hand, flowable, fast-curing materials, such as cavity liners may be simply brushed on the surface of the treated tooth.

Dental materials such as restoratives, sealers, bonding agents, cements and orthodontic adhesives containing in their resin part 20-90% of the dimethacrylate of the present invention exhibit most desirable properties, especially in respect to color stability, low water sorption, high mechanical strength and low polymerization shrinkage. The following examples describe certain embodiments of the invention. It is to be understood that these examples are given only to illustrate the nature of the invention and should not, in any way, be understood as limiting the scope of this invention, defined in the claims.

EXAMPLE 1

200 g of bis(hydroxymethyl)tricyclo[5.2.1.0$^{2,6}$]decane (TCD alcohol DN, a tradename of Hoechst), believed to be a mixture of 3,8-bis(hydroxymethyl)tricyclo[5.2.1.0$^{2,6}$]decane and 4,9-bis(hydroxymethyl)tricyclo[5.2.1.0$^{2,6}$]decane, were mixed with 300 g of adipic acid, 200 g of toluene and 1.2 g of dibutyltin diacetate in a reaction flask equipped with a water condenser, stirrer and water trap and heated to a temperature of 115°-125° C. This temperature was maintained until 32.5 ml of water was collected in the trap. From this synthesized diadipate ester, the toluene was removed by distillation and 1.5 g of BHT, 1.8 g of triphenylphosphine and 0.06 g of hydroquinone were added. The mixture was heated to 100° C. and 340 g of glycidyl methacrylate was introduced over the period of 3 hours while stirring and maintaining a temperature of 100°-105° C. After the introduction of glycidyl methacrylate is complete, the stirring and heating is maintained until the acid number of the reaction mixture is 4 or less. The product constitutes a light yellow liquid having a refractive index $n_D^{40}$ 1.485.

EXAMPLE 2

A composite restorative material has been formulated of:

| Part A | Part B |
|---|---|
| Powdered Quartz - 350 parts | Powdered Quartz - 350 parts |
| Powdered Glass - 150 parts | Powdered Glass - 150 parts |
| Methacroylpropyl trihydroxysilane - 5 parts | Methacroylpropyl trihydroxysilane - 5 parts |
| Benzoyl Peroxide - 3 parts | N,N—bis(2-hydroxyethyl)-p-toluidine - 4 parts |
| Resin as described in Example 1 - 80 parts | Cyasorb UV-9 - 1 part |
| Hexanediol dimethacrylate - 20 parts | EBA - 66 parts |
| | Bis-GMA - 12 parts |
| | Triethylene glycol dimethacrylate - 22 parts |

Parts A and B when mixed together in about equal amounts cured in 150 seconds at 23° C. producing material having the following properties:

| Water Sorption at 37° C. | .4 mg/cm$^2$ |
|---|---|
| Diametral Tensile Strength | 6,000 psi |
| Compressive Strength | 42,000 psi |
| Hardness (Barcol) | 100 |

This material also exhibited an excellent color stability, resistance to staining, and optical properties most desirable from the standpoint of dental aesthetics.

EXAMPLE 3

A composite restorative has been formulated using components as described in Example 2 except that said resin component of the formulation was the reaction product of one mole of the monomer described in Example 1 per 1.2 moles of n-butylisocyanate. The properties of the cured materials were virtually identical to those described in Example 2.

EXAMPLE 4

A polymerizable dental resin suitable for use as a fissure sealer for preventing occlusal carries and as a bonding agent for improving marginal adaption of restoratives to tooth structure and to improve adhesive bond to etched tooth enamel has been formulated using:
  40% monomer described in Example 1
  10% of Bis-GMA monomer and
  50% of hexanediol dimethacrylate
The resin blend as described above could be cured either by chemical means using benzoyl peroxide/aromatic tertiary amine polymerization initiating system or by ultraviolet or visible light using known light activated polymerization initiators such as benzoin, benzoin methyl ether, benzil and other commercially available photoinitiators.

While the use of the monomers of the present invention has been described primarily with respect to dental materials, particularly composite restorative materials, it is noted that these monomers may also be used in other materials such as bone cements and UV curable inks. Thus, while certain representative embodiments and details have been shown for the purpose of illustrating the invention, it will be apparent to those skilled in the art that various changes and modifications may be made therein without departing from the spirit or scope of the invention. It will be further understood that the invention may comprise, consist essentially of or consist of the steps or materials recited herein.

What is claimed is:

1. A dental material comprising polymerizable unsaturated material comprising at least about 10% by weight of a dimethacrylate monomer having the following chemical structure:

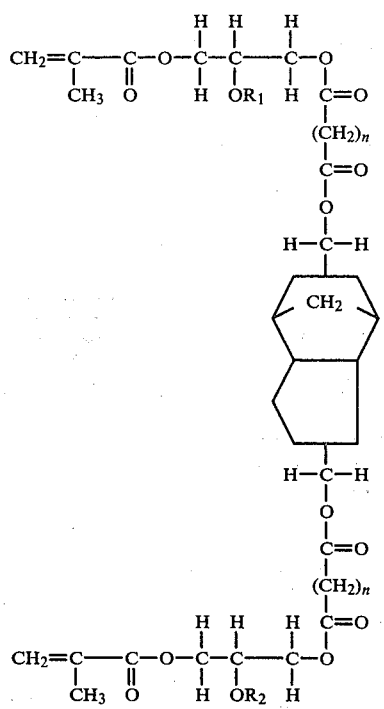

where n represents a number of 2 to 8;

$R_1$ and $R_2$ are the same or different and are hydrogen or one or more groups of the formula:

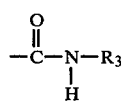

where $R_3$ is an aliphatic group of 1-14 carbon atoms, aromatic group of 6 to 14 carbon atoms or cycloaliphatic group having 3 to 14 carbon atoms and at least one of $R_1$ and $R_2$ is

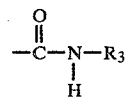

the remainder of said polymerizable material being at least 10% by weight of at least one acrylic or methacrylic monomer acceptable for oral application associated with dental treatment.

2. A dental material according to claim 1, wherein said polymerizable unsaturated material comprises about 20 to about 90% by weight of said dimantacrylate monomer and about 10 to about 80% by weight of at least one other polymethacrylate suitable for use in dental materials.

3. A dental material according to claim 2, wherein said other polymethacrylate is selected from the group consisting of diethylene glycol dimethacrylate, triethylene glycol dimethacrylate, tetraethylene glycol dimethacrylate, 1,6-hexanediol dimethacrylate, trimethylolpropane trimethacrylate, 2,2-bis[4'(3''-methacroyl-2''-hydroxypropoxy)phenyl]propane, 2,2-bis[4'(2''-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate and 2,2 bis-(4'-methacroylphenyl)propane.

4. A dental material according to claim 1 comprising two parts capable of curing upon mixing of these parts, one of said parts comprising a peroxide-type polymerization initiator and the other of said parts comprising a tertiary aromatic amine-type activator.

5. A dental material according to claim 1 comprising a light activated polymerization initiator capable of curing said dental material upon irradiation with ultraviolet or visible light.

6. A composite dental restorative material comprising glass or ceramic filler and polymerizable material,
said polymerizable material comprising at least one first monomer and at least one second monomer,
said first monomer being the dimethacrylate monomer according to claim 1,
said second monomer being a diluent selected from the group consisting of di- and trimethacrylates having from 10 to 18 carbon atoms,
said diluent further being selected from the group consisting of alkylene glycol dimethacrylates, polyalkylene glycol dimethacrylates and alkanetriol trimethacrylates,
said at least one first monomer constituting at least 20% by weight of said polymerizable material,
said at least one second monomer constituting at least 10% by weight of said polymerizable material, and the weight ratio of said filler to said polymerizable material being from about 1.5:1 to about 8.5:1.

7. A composite restorative material according to claim 6, wherein said polymerizable material further comprises at least one third monomer selected from the group consisting of 2,2-bis[4'(3''-methacroyl-2''-hydroxypropoxy)phenyl]propane, 2,2-bis(4'(2''-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate and 2,2-bis(4'-methacroylphenyl)propane, the weight ratio of said first monomer to said third monomer being from about 7:9 to 9:7.

8. A composite restorative material according to claim 7, wherein:
   (i) said at least one first monomer and said at least one third monomer each constitute from about 35% to about 45% by weight of said polymerizable material, provided that the total amount of said at least one first monomer plus said at least one third monomer constitutes from about 75% to about 85% by weight of said polymerizable material;
   (ii) said at least one second monomer constitutes from about 15% to about 25% by weight of said polymerizable material; and
   (iii) said ratio of said filler to said polymerizable material is from about 4:1 to about 6:1.

9. A composite restorative material according to claim 6 wherein the weight ratio of said filler to said polymerizable material is from about 1.5:1 to about 6.5:1.

10. A composite restorative material according to claim 9 wherein polymerizable material further comprises at least one third monomer selected from the group consisting of 2,2-bis(4'(3''-methacroyl-2''-hydroxypropoxy)phenyl]propane, 2,2-bis[4'(2''-methacroylethoxy)phenyl]propane, 2-methacroylethyl-3-methacroyl-2-hydroxypropyl tetrahydrophthalate, 2-methacroylethyl-3-methacroyl-2-hydroxypropyl hexahydrophthalate and 2,2-bis(4'-methacroylphenyl)propane, the weight ratio of said first monomer to said third monomer being from about 7:9 to about 9:7.

11. A method for forming a hardened substance on teeth comprising the steps of:
   (i) applying to said teeth a dental material comprising a polymerizable material, said polymerizable material comprising at least 10% by weight of the dimethacrylate monomer of claim 7; and
   (ii) polymerizing said polymerizable material in situ.

12. A method for forming a hardened substance on teeth comprising the steps of:
   (i) applying to said teeth a dental material comprising a polymerizable material, said polymerizable material comprising at least 10% by weight of the compound of the following chemical structure:

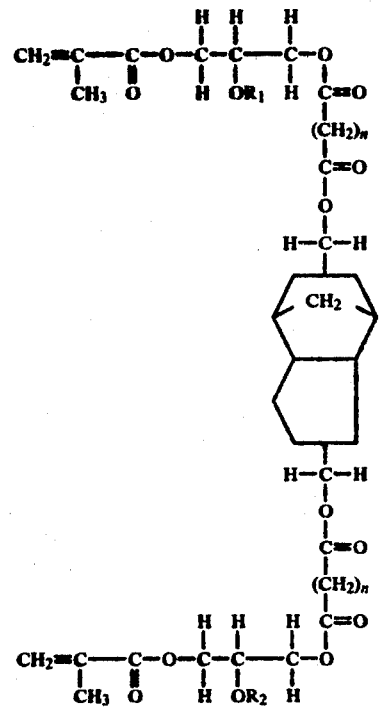

where
n represents a number of 2 to 8;
$R_1$ and $R_2$ are the same or different and are hydrogen or one or more groups of the formula:

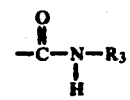

where
$R_3$ is an aliphatic group of 1–14 carbon atoms, aromatic group of 6 to 14 carbon atoms or cycloaliphatic group having 3 to 14 carbon atoms; and
(ii) polymerizing said polymerizable material in situ.

13. A method according to claim 12 where $R_1$ and $R_2$ are both hydrogen.

* * * * *